United States Patent
Shipley et al.

(10) Patent No.: US 10,456,254 B2
(45) Date of Patent: *Oct. 29, 2019

(54) TRANSCATHETER PROSTHETIC HEART VALVE DELIVERY SYSTEM WITH RECAPTURING FEATURE AND METHOD

(71) Applicant: Medtronic, Inc., Minneapolis, MN (US)

(72) Inventors: Adam Shipley, San Rafael, CA (US); John P. Shanahan, Santa Rosa, CA (US); Andrew Crisman, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 228 days.

This patent is subject to a terminal disclaimer.

(21) Appl. No.: 15/346,843

(22) Filed: Nov. 9, 2016

(65) Prior Publication Data

US 2017/0049569 A1 Feb. 23, 2017

Related U.S. Application Data

(60) Continuation of application No. 14/641,679, filed on Mar. 9, 2015, now Pat. No. 9,522,063, which is a division of application No. 12/757,138, filed on Apr. 9, 2010, now Pat. No. 8,998,980.

(51) Int. Cl.
*A61F 2/24* (2006.01)
*A61F 2/95* (2013.01)

(52) U.S. Cl.
CPC ............ *A61F 2/2436* (2013.01); *A61F 2/243* (2013.01); *A61F 2/2418* (2013.01); *A61F 2/2427* (2013.01); *A61F 2002/9517* (2013.01); *A61F 2002/9534* (2013.01)

(58) Field of Classification Search
CPC ...... A61F 2002/9517; A61F 2002/9534; A61F 2/2436; A61F 2002/9522; A61F 2/243; A61F 2/95
USPC ....... 606/108, 191, 194, 198, 200; 623/1.11, 623/2.1, 2.11, 2.12
See application file for complete search history.

(56) References Cited

U.S. PATENT DOCUMENTS

| | | | |
|---|---|---|---|
| 5,683,451 A | 11/1997 | Lenker et al. | |
| 5,824,041 A | 10/1998 | Lenker et al. | |
| 5,906,619 A | 5/1999 | Olson et al. | |

(Continued)

FOREIGN PATENT DOCUMENTS

| | | |
|---|---|---|
| GB | 2433700 | 7/2007 |
| WO | 2008/138584 | 11/2008 |

(Continued)

*Primary Examiner* — Katherine M Shi
(74) *Attorney, Agent, or Firm* — Dicke, Billig & Czaja, PLLC

(57) ABSTRACT

A delivery system for percutaneously deploying a prosthetic heart valve. The system includes an inner shaft assembly, a delivery sheath capsule and a handle maintaining a first actuator and a second actuator. The capsule is configured to compressively retain the prosthetic heart valve over the inner shaft assembly. The first actuator is operated to proximally retract the delivery sheath capsule and expose the prosthetic heart valve relative to the capsule. The second actuator is operated to proximally retract the prosthetic heart valve by transmitting forces to the inner shaft assembly.

19 Claims, 4 Drawing Sheets

(56) References Cited

U.S. PATENT DOCUMENTS

| | | | |
|---|---|---|---|
| 5,957,949 A | 9/1999 | Leonhardt et al. | |
| 7,052,511 B2 | 5/2006 | Weldon et al. | |
| 2003/0199963 A1 | 10/2003 | Tower et al. | |
| 2004/0230284 A1 | 11/2004 | Headley et al. | |
| 2005/0137688 A1 | 6/2005 | Salahieh et al. | |
| 2006/0004439 A1 | 1/2006 | Spenser et al. | |
| 2006/0052867 A1 | 3/2006 | Revuelta et al. | |
| 2006/0229659 A1* | 10/2006 | Gifford | A61B 17/22012 606/200 |
| 2006/0259136 A1 | 11/2006 | Nguyen et al. | |
| 2006/0265056 A1 | 11/2006 | Nguyen et al. | |
| 2007/0005131 A1 | 1/2007 | Taylor | |
| 2007/0088431 A1 | 4/2007 | Bourang et al. | |
| 2007/0239266 A1 | 10/2007 | Birdsall | |
| 2007/0239269 A1 | 10/2007 | Dolan et al. | |
| 2007/0270932 A1 | 11/2007 | Headley et al. | |
| 2008/0065011 A1 | 3/2008 | Marchand et al. | |
| 2008/0082165 A1 | 4/2008 | Wilson et al. | |
| 2008/0147160 A1 | 6/2008 | Ghione et al. | |
| 2008/0147181 A1 | 6/2008 | Ghione et al. | |
| 2008/0147182 A1 | 6/2008 | Righini et al. | |
| 2008/0188928 A1 | 8/2008 | Salahieh et al. | |
| 2008/0208320 A1 | 8/2008 | Tan-Malecki et al. | |
| 2009/0093876 A1 | 4/2009 | Nitzan et al. | |
| 2009/0118740 A1 | 5/2009 | Mangiardi et al. | |
| 2009/0138079 A1 | 5/2009 | Tuval et al. | |
| 2009/0171447 A1 | 7/2009 | von Segesser et al. | |
| 2009/0171456 A1* | 7/2009 | Kveen | A61F 2/2418 623/2.11 |
| 2009/0177275 A1 | 7/2009 | Case | |
| 2009/0192518 A1 | 7/2009 | Golden et al. | |
| 2009/0281619 A1 | 11/2009 | Le et al. | |
| 2010/0094411 A1 | 4/2010 | Tuval et al. | |
| 2010/0121434 A1 | 5/2010 | Paul et al. | |

FOREIGN PATENT DOCUMENTS

| | | |
|---|---|---|
| WO | 2009/091509 | 7/2009 |
| WO | 2011/035327 | 3/2011 |

* cited by examiner

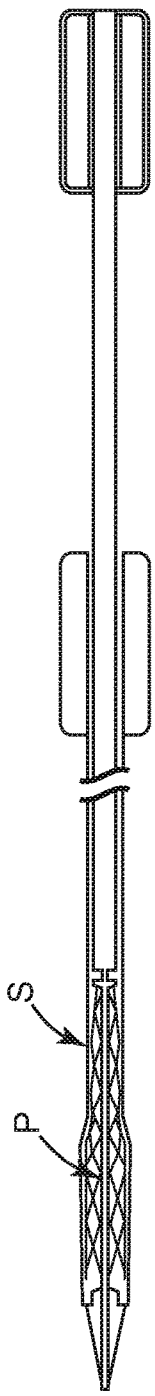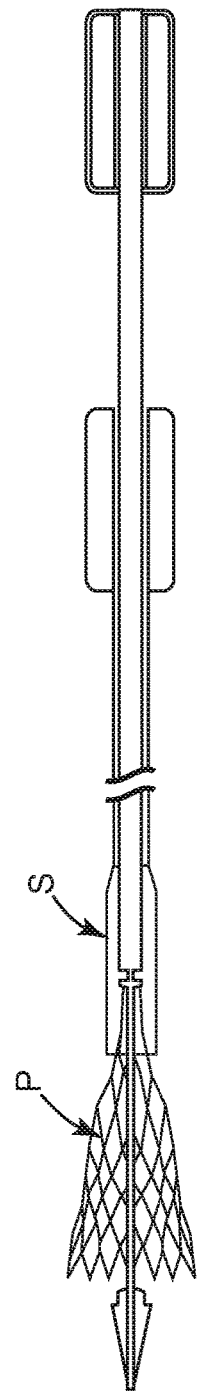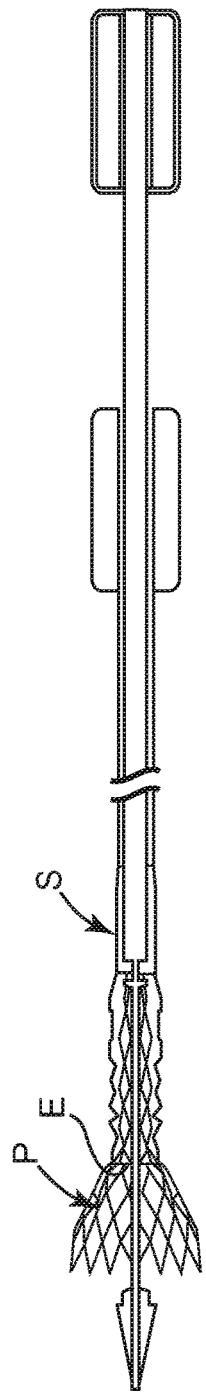
Fig. 1A PRIOR ART
Fig. 1B PRIOR ART
Fig. 1C PRIOR ART

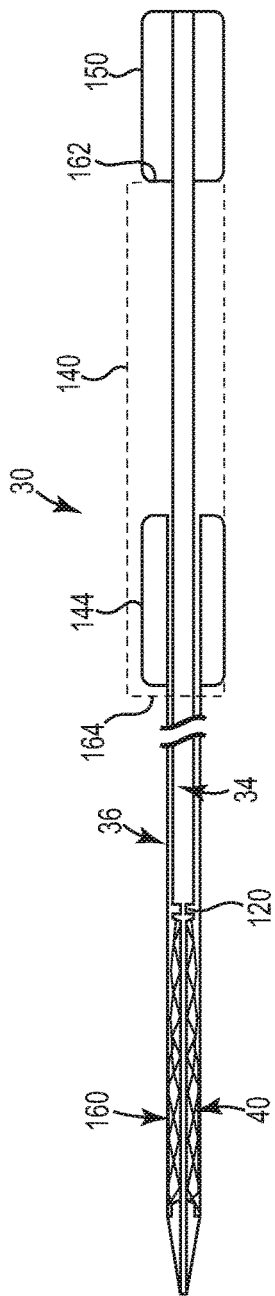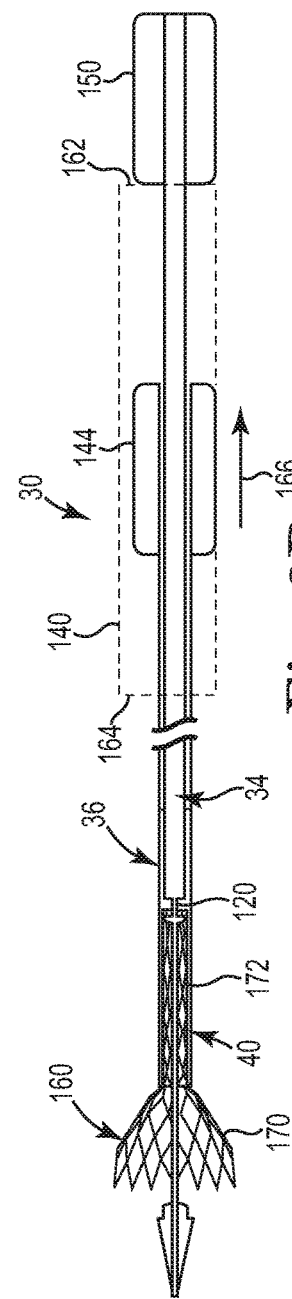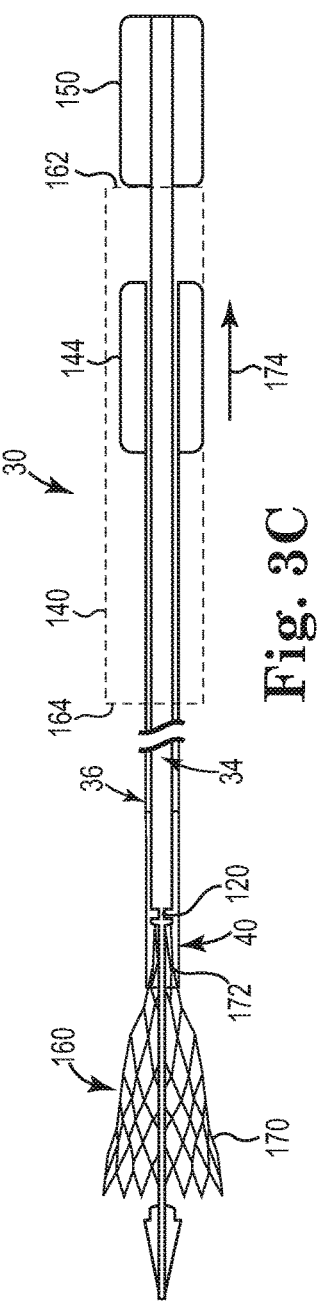

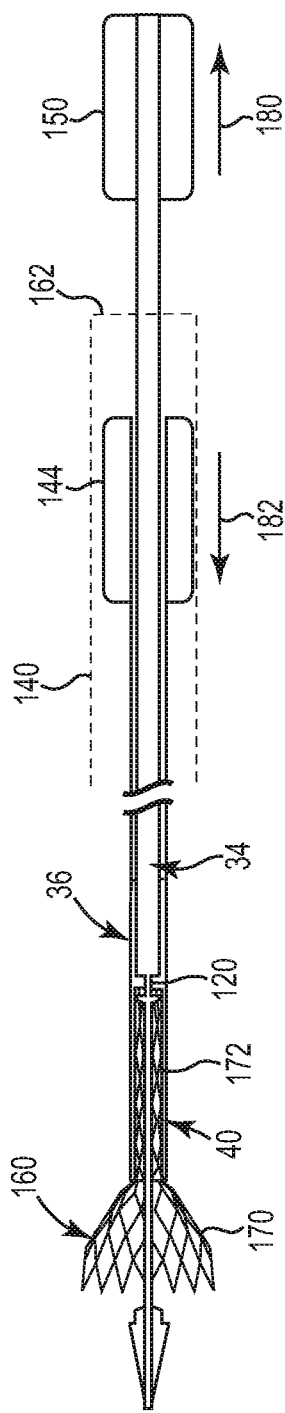
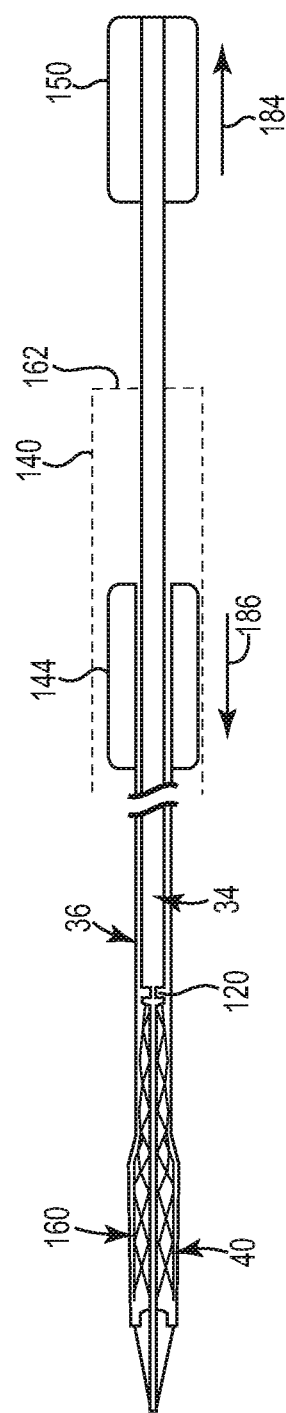

ated with the use of the heart-lung bypass machine, for example.
TRANSCATHETER PROSTHETIC HEART VALVE DELIVERY SYSTEM WITH RECAPTURING FEATURE AND METHOD

RELATED APPLICATIONS

This application is a Continuation of and claims the benefit of U.S. patent application Ser. No. 14/641,679, filed Mar. 9, 2015, which is a Division of and claims the benefit of U.S. patent application Ser. No. 12/757,138 filed Apr. 9, 2010, now U.S. Pat. No. 8,998,980. The disclosures of which are herein incorporated by reference in their entirety.

BACKGROUND

The present disclosure relates to systems and methods for percutaneous implantation of a heart valve prosthesis. More particularly, it relates to systems and methods for transcatheter implantation of a stented prosthetic heart valve, including partial deployment, recapturing, and repositioning of the prosthesis at the implantation site.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With these percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of a relatively more complex prosthetic heart valve.

Various types and configurations of prosthetic heart valves are available for percutaneous valve procedures, and continue to be refined. The actual shape and configuration of any particular prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation systems, the stent frame of the valved stent is made of a self-expanding material and construction. With these systems, the valved stent is crimped down to a desired size and held in that compressed arrangement within an outer sheath, for example. Retracting the sheath from the valved stent allows the stent to self-expand to a larger diameter, such as when the valved stent is in a desired position within a patient. In other percutaneous implantation systems, the valved stent can be initially provided in an expanded or uncrimped condition, then crimped or compressed on a balloon portion of catheter until it is as close to the diameter of the catheter as possible. Once delivered to the implantation site, the balloon in inflated to deploy the prosthesis. With either of these types of percutaneous stent delivery systems, conventional sewing of the prosthetic heart valve to the patient's native tissue is typically not necessary.

It is imperative that the stented prosthetic heart valve be accurately located relative to the native annulus immediately prior to full deployment from the catheter as successful implantation requires the prosthetic heart valve intimately lodge and seal against the native annulus. If the prosthesis is incorrectly positioned relative to the native annulus, serious complications can result as the deployed device can leak and may even dislodge from the native valve implantation site. As a point of reference, this same concern does not arise in the context of other vascular stents; with these procedures, if the target site is "missed," another stent is simply deployed to "make-up" the difference.

While imaging technology can be employed as part of the implantation procedure to assist a clinician in better evaluating a location of the transcatheter prosthetic heart valve immediately prior to deployment, in many instances, this evaluation alone is insufficient. Instead, clinicians desire the ability to partially deploy the prosthesis, evaluate a position relative to the native annulus, and reposition the prosthesis prior to full deployment if deemed necessary. Repositioning, in turn, requires the prosthesis first be re-compressed and re-located back within the outer delivery sheath. Stated otherwise, the partially deployed stented prosthetic heart valve must be "recaptured" by the delivery system, and in particular within the outer sheath. While, in theory, the recapturing of a partially deployed stented prosthetic heart valve is straight forward, in actual practice, the constraints presented by the implantation site and the stented heart valve itself render the technique exceedingly difficult.

For example, the stented heart valve is purposefully designed to rigidly resist collapsing forces once deployed to properly anchor itself in the anatomy of the heart. Thus, whatever tooling is employed to force a partially-deployed segment of the prosthesis back to a collapsed arrangement must be capable of exerting a significant radial force. Conversely, however, the tooling cannot be overly rigid to avoid damaging the transcatheter heart valve as part of a recapturing procedure. Along these same lines, the aortic arch must be traversed, necessitating that the delivery system provide sufficient articulation attributes. Unfortunately, existing delivery systems do not consider, let alone optimally address, these and other issues.

As mentioned above, an outer sheath or catheter is conventionally employed to deliver a self-deploying vascular stent. Applying this same technique for the delivery of a self-deploying stented prosthetic heart valve, the high radial expansion force associated with the prosthesis is not problematic for complete deployment as the outer sheath is simply retracted in tension to allow the prosthetic heart valve to deploy. Were the conventional delivery system operated to only partially withdraw the outer sheath relative to the prosthesis, only the so-exposed distal region of the prosthetic would expand while the proximal region remains coupled to the delivery system. In theory, the outer sheath could simply be advanced distally to recapture the expanded region. Unfortunately, with conventional sheath configurations, attempting to compress the expanded region of the stented prosthetic heart valve by distally sliding the sheath is unlikely to be successful. The conventional delivery sheath cannot readily overcome the radial force of the expanded region of the prosthesis because, in effect, the sheath is placed into compression and will collapse due at least in part to the abrupt edge of the sheath being unable to cleanly slide over the expanded region of the prosthesis. This effect is illustrated in a simplified form in FIGS. 1A-1C. Prior to deployment (FIG. 1A), the stented prosthetic heart valve P is constrained within, and supports, the sheath S. With deployment (FIG. 1B), the sheath S is distally retracted, and the prosthesis P partially deploys. Where an attempt made to "recapture" the prosthesis P by distally sliding the sheath (FIG. 1C), a leading end E of the sheath S abruptly abuts against the enlarged diameter of the prosthesis P, such that the distal end E cannot readily slide over the prosthesis P. Further, the sheath S is no longer internally supported and the radially expanded bias of the prosthesis P causes the sheath S to buckle or collapse.

In light of the above, a need exists for a stented transcatheter prosthetic heart valve delivery system and method that satisfies the constraints associated with heart valve implantation and permits partial deployment and recapturing of the prosthesis.

SUMMARY

Some aspects in accordance with principles of the present disclosure relate to a delivery system for percutaneously deploying a prosthetic heart valve. The prosthetic heart valve is radially self-expandable from a compressed arrangement to a natural arrangement. The delivery system includes an inner shaft assembly, a delivery sheath capsule, and a handle maintaining a first actuator coupled to the delivery sheath capsule and a second actuator coupled to the inner shaft assembly. The inner shaft assembly includes an intermediate region providing a coupling structure configured to selectively engage a prosthetic heart valve. The delivery sheath capsule is slidably disposed over the inner shaft assembly and is configured to compressively retain the prosthetic heart valve engaged with the coupling structure. With this construction, the delivery system is configured to provide a loaded state in which the capsule compressively retains the prosthetic heart valve over the inner shaft assembly. During use, the first actuator can be operated to facilitate sliding of the capsule relative to the prosthetic heart valve so as to at least partially deploy the prosthetic heart valve relative to the delivery sheath capsule. The second actuator is operated to apply proximal forces to the inner shaft assembly and the prosthetic heart valve relative to the delivery system to facilitate recapture of the prosthetic heart valve.

Yet other aspects in accordance with principles of the present disclosure relate to a device for repairing a heart valve of a patient. The device includes a delivery system and a prosthetic heart valve. The delivery system includes the inner shaft assembly, the delivery sheath capsule, and the handle, including the first actuator and the second actuator, as described above. The prosthetic heart valve has a frame and a valve structure forming at least two valve leaflets attached to the frame. With this construction, the prosthetic heart valve is self-expandable from a compressed arrangement to a natural arrangement. With this construction, the device is configured to be transitionable between a loaded state, a partially deployed state, and a recapturing state. In the loaded state, the prosthetic heart valve is coupled to the intermediate region of the inner shaft assembly, with the capsule compressively retaining the prosthetic heart valve in the compressed arrangement. In the partially deployed state, the capsule is at least partially withdrawn from the prosthetic heart valve using the first actuator such that a distal region of the prosthetic heart valve is exposed relative to the capsule and self-expands. In the recapturing state, the second actuator is operated to position the delivery system along the distal exposed region of the prosthetic heart valve and surround the prosthetic heart valve, due to proximal forces placed on the inner shaft assembly using the second actuator.

Yet other aspects in accordance with principles of the present disclosure relate to a method of deploying a prosthetic heart valve to an implantation site. The method includes receiving a delivery system loaded with a radially expandable prosthetic heart valve having a frame to which a valve structure is attached. The delivery system includes a delivery sheath capsule compressively containing the prosthetic heart valve in a compressed arrangement over an inner shaft assembly in a loaded state. The prosthetic heart valve is delivered, in the compressed arrangement, through a bodily lumen of the patient and to the implantation site via the delivery system in the loaded state. The capsule is proximally retracted relative to the prosthetic heart valve such that a distal region of the prosthetic heart valve is exposed distal the capsule. The exposed, distal region self-expands toward a deployed arrangement. A position of the partially deployed prosthetic heart valve relative to the implantation site is evaluated. Based upon the evaluation, the prosthetic heart valve is proximally advanced relative to the delivery system such that the delivery system is advanced over the prosthetic heart valve.

BRIEF DESCRIPTION OF THE DRAWINGS

FIGS. 1A-1C are simplified side views illustrating deficiencies of existing delivery sheaths or catheters to effectuate recapture of a partially deployed prosthetic heart valve;

FIGS. 3A-3E are simplified, cross-sectional views illustrating use of the delivery system of FIG. 2 in implanting a prosthetic heart valve, including partial deployment and repositioning thereof.

DETAILED DESCRIPTION

Figure 2:
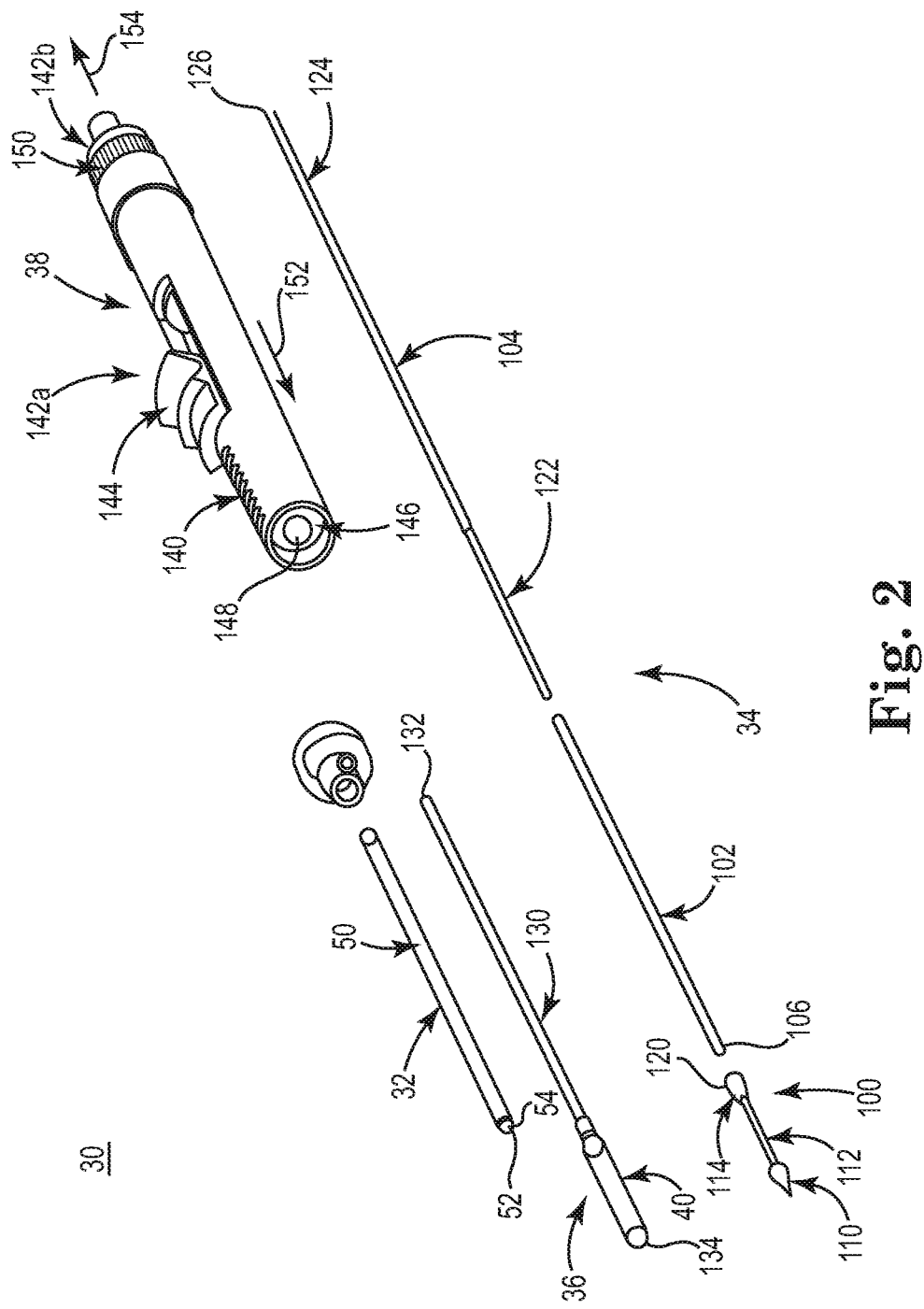
FIG. 2 is an exploded, perspective view of a delivery system in accordance with principles of the present disclosure and useful for percutaneously delivering a prosthetic heart valve to a heart valve implantation site.

Current transcatheter heart valve delivery systems do not have the capability of transcatheter valve repositioning in the antegrade or retrograde directions after deployment. The delivery systems of the present disclosure overcome these problems, and permit the clinician to partially deploy the prosthetic heart valve, and prior to release, reposition or recapture and remove it. In general terms, the system functions by providing an actuator that serves to retract (i.e., by providing a proximal force thereto) a partially deployed prosthesis to effectuate recapturing of the partially deployed prosthetic heart valve.

As referred to herein, the prosthetic heart valve as used in accordance with the various systems, devices, and methods of the present disclosure may include a wide variety of different configurations, such as a bioprosthetic heart valve having tissue leaflets or a synthetic heart valve having a polymeric, metallic, or tissue-engineered leaflets, and can be specifically configured for replacing any heart valve. Thus, the prosthetic heart valve useful with the systems, devices, and methods of the present disclosure can be generally used for replacement of a native aortic, mitral, pulmonic, or tricuspid valves, for use as a venous valve, or to replace a failed bioprosthesis, such as in the area of an aortic valve or mitral valve, for example.

In general terms, the prosthetic heart valves of the present disclosure include a frame maintaining a valve structure (tissue or synthetic), with the frame having a normal, expanded arrangement and collapsible to a compressed arrangement for loading within the delivery system. The frame is normally constructed to self-deploy or self-expand when released from the delivery system. For example, the prosthetic heart valve useful with the present disclosure can be a prosthetic valve sold under the trade name CoreValve® available from Medtronic CoreValve, LLC. Other non-limiting examples of transcatheter heart valve prostheses useful with systems and methods of the present disclosure are described in U.S. Publication Nos. 2006/0265056; 2007/0239266; and 2007/0239269, the teachings of each which are incorporated herein by reference.

The frames are support structures that comprise a number of struts or wire portions arranged relative to each other to provide a desired compressibility and strength to the prosthetic heart valve. In general terms, the frames of the present disclosure are generally tubular support structures having an internal area in which valve structure leaflets will be secured. The leaflets can be formed from a verity of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the frame. In another alternative, the frame and leaflets can be fabricated at the same time, such as may be accomplished using high-strength nano-manufactured NiTi films produced at Advance BioProsthetic Surfaces (ABPS), for example. The frame support structures are generally configured to accommodate at least two (typically three) leaflets; however, replacement prosthetic heart valves of the types described herein can incorporate more or less than three leaflets.

Some embodiments of the frames can be a series of wires or wire segments arranged such that they are capable of self-transitioning from a collapsed arrangement to a normal, radially expanded arrangement. In some constructions, a number of individual wires comprising the frame support structure can be formed of a metal or other material. These wires are arranged in such a way that the frame support structure allows for folding or compressing or crimping to the compressed arrangement in which the internal diameter is smaller than the internal diameter when in the natural, expanded arrangement. In the collapsed arrangement, such a frame support structure with attached valves can be mounted onto a delivery system. The frame support structures are configured so that they can be changed to their natural, expanded arrangement when desired, such as by the relative movement of one or more sheaths relative to a length of the frame.

The wires of these frame support structures in embodiments of the present disclosure can be formed from a shape memory material such as a nickel titanium alloy (e.g., Nitinol™). With this material, the support structure is self-expandable from the compressed arrangement to the natural, expanded arrangement, such as by the application of heat, energy, and the like, or by the removal of external forces (e.g., compressive forces). This frame support structure can also be compressed and re-expanded multiple times without damaging the structure of the frame. In addition, the frame support structure of such an embodiment may be laser-cut from a single piece of material or may be assembled from a number of different components. For these types of frame structures, one example of a delivery system that can be used includes a catheter with a retractable sheath that covers the frame until it is to be deployed, at which point the sheath can be retracted to allow the frame to self-expand. Further details of such embodiments are discussed below.

With the above in mind, one embodiment of a transcatheter stented prosthetic heart valve delivery system 30 is shown in FIG. 2. The system 30 generally includes a stability layer 32, an inner shaft assembly 34, a delivery sheath assembly 36, and a handle 38. Details on the various components are provided below. In general terms, however, the delivery system 30 provides a loaded state in which a prosthetic heart valve (not shown) is coupled to the inner shaft assembly 34 and compressively retained within a capsule 40 of the delivery sheath assembly 36. The delivery sheath assembly 36 can be manipulated to withdraw the capsule 40 proximally from the prosthetic heart valve via operation of the handle 38, permitting the prosthesis to self-expand and release from the inner shaft assembly 34. Further, the handle 38 can be operated to maneuver the inner shaft assembly 34 relative to the delivery sheath assembly 36 to position the capsule 40 over a partially deployed region of the prosthetic heart valve to facilitate recapturing of the prosthesis within the capsule 40. In particular, proximal forces can be applied to inner shaft assembly 34 in order to facilitate recapture of the prosthetic heart valve. As a point of reference, various features of the components 32-38 reflected in FIG. 2 and described below can be modified or replaced with differing structures and/or mechanisms. Thus, the present disclosure is in no way limited to the stability layer 32, the inner shaft assembly 34, the delivery sheath assembly 36, the handle 38, etc., as shown and described below. More generally, delivery systems in accordance with the present disclosure provide features capable of compressively retaining a self-deploying, stented prosthetic heart valve (e.g., the capsule 40), a mechanism capable of effectuating release or deployment of the prosthesis (e.g., retracting the capsule 40), and an actuator (e.g., associated with handle 38) that retracts the prosthesis to promote recapture.

The stability layer 32 illustratively includes a shaft 50, which forms a lumen 52 (referenced generally) sized to be slidably received over the inner shaft assembly 34, terminating at a distal end 54. The shaft 50 can take many forms and in general provides structural integrity to system 30, yet allowing sufficient flexibility to maneuver the capsule 40 to a target site (e.g., the aortic valve). To this end, shaft 50, in one embodiment, is formed of a polymeric material with an associated reinforcement layer. In other embodiments, the stability layer 32 can be eliminated. In yet other embodiments, stability layer 32 can facilitate recapture by providing columnar strength support to recapture the prosthetic heart valve, for example, by sliding over capsule 40 or within capsule 40. In other embodiments, when stability layer 32 is configured to promote recapture, the stability layer 32 can be equipped to form a funnel shape at its distal end to recapture the prosthetic heart valve.

Returning to FIG. 2, the remaining components 34-38 of the delivery system 30 can assume a variety of forms appropriate for percutaneously delivering and deploying a self-expanding prosthetic heart valve. For example, the inner shaft assembly 34 can have various constructions appropriate for supporting a prosthetic heart valve within the capsule 40. In some embodiments, the inner shaft assembly 34 can include a retention member 100, an intermediate tube 102, and a proximal tube 104. In general terms, the retention member 100 can be akin to a plunger, and incorporates features for retaining the stented prosthetic heart valve within the capsule 40 as described below. The tube 102 connects the retention member 100 to the proximal tube 104, with the proximal tube 104, in turn, coupling the inner shaft assembly 34 with the handle 38. The components 100-104 can combine to define a continuous lumen 106 (referenced generally) sized to slidably receive an auxiliary component such as a guide wire (not shown).

The retention member 100 can include a tip 110, a support tube 112, and a hub 114. The tip 110 forms or defines a nose cone having a distally tapering outer surface adapted to promote atraumatic contact with bodily tissue. The tip 110 can be fixed or slidable relative to the support tube 112. The support tube 112 extends proximally from the tip 110 and is configured to internally support a compressed prosthetic heart valve generally disposed thereover, and has a length and outer diameter corresponding with dimensional attributes of the selected prosthetic heart valve. The hub 114 is attached to the support tube 112 opposite the tip 110 (e.g., an adhesive bond), and provides a coupling structure 120 (referenced generally) configured to selectively capture a corresponding feature of the prosthetic heart valve. The coupling structure 120 can assume various forms, and is generally located along an intermediate portion of the inner shaft assembly 34. In some constructions, the coupling structure 120 includes one or more fingers sized to be received within corresponding apertures formed by the prosthetic heart valve frame (e.g., the prosthetic heart valve frame can form wire loops at a proximal end thereof that are received over respective ones of the fingers when compressed within the capsule 40).

The intermediate tube 102 is formed of a flexible polymer material (e.g., PEEK), and is sized to be slidably received within the delivery sheath assembly 36. The proximal tube 104 can include, in some embodiments, a leading portion 122 and a trailing portion 124. The leading portion 122 serves as a transition between the intermediate and proximal tubes 102, 104 and thus in some embodiments is a flexible polymer tubing (e.g., PEEK) having a diameter slightly less than that of the intermediate tube 102. The trailing portion 124 has a more rigid construction, configured for robust assembly with the handle 38 such as a metal hypotube, at a proximal end 126. Other constructions are also envisioned. For example, in other embodiments, the intermediate and proximal tubes 102, 104 are integrally formed as a single, homogenous tube or solid shaft.

The delivery sheath assembly 36 includes the capsule 40 and a delivery sheath shaft 130, and defines proximal and distal ends 132, 134. The capsule 40 extends distally from the delivery shaft 130, and in some embodiments has a more stiffened construction (as compared to a stiffness of the delivery shaft 130) that exhibits sufficient radial or circumferential rigidity to overtly resist the expected expansive forces of the prosthetic heart valve in the compressed arrangement. For example, the delivery shaft 130 can be a polymer tube embedded with a metal braiding, whereas the capsule 40 is a laser-cut metal tube. Alternatively, the capsule 40 and the delivery shaft 130 can have a more uniform construction (e.g., a continuous polymer tube). Regardless, the capsule 40 is constructed to compressively retain the prosthetic heart valve at a predetermined diameter when loaded within the capsule 40, and the delivery shaft 130 serves to connect the capsule 40 with the handle 38. The delivery shaft 130 (as well as the capsule 40) is constructed to be sufficiently flexible for passage through a patient's vasculature, yet exhibit sufficient longitudinal rigidity to effectuate desired axial movement of the capsule 40. In other words, proximal retraction of the delivery shaft 130 is directly transferred to the capsule 40 and causes a corresponding proximal retraction of the capsule 40. In other embodiments, the delivery shaft 130 is further configured to transmit a rotational force or movement onto the capsule 40.

The handle 38 generally includes a housing 140 and one or more actuator mechanisms (i.e., controls) 142 (referenced generally). The housing 140 maintains the actuator mechanism(s) 142, with the handle 38 configured to facilitate sliding movement of the delivery sheath assembly 36 relative to the inner shaft assembly 34, as well as provide proximal forces to the inner shaft assembly 34 relative to the delivery sheath assembly 36 so as to retract the prosthetic heart valve into the capsule 40. The housing 140 can have any shape or size appropriate for convenient handling by a user. In one simplified construction, a first, deployment actuator mechanism 142a includes a user interface or actuator (e.g., a deployment actuator) 144 slidably retained by the housing 140 and coupled to a delivery sheath connector body 146. The proximal end 132 of the delivery sheath assembly 36 is connected to the delivery sheath connector body 146.

The inner shaft assembly 34, and in particular the proximal tube 104, is slidably received within a passage 148 (referenced generally) of the delivery sheath connector body 146, and is rigidly coupled to the housing 140 at proximal end 126. A second, recapture actuator mechanism 142b (referenced generally) similarly includes a user interface or actuator (e.g., a recapture actuator) 150 slidably maintained by the housing 140 and coupled to the inner shaft assembly 34 via one or more bodies (not shown), facilitating movement of the inner shaft assembly 34 with operation of the recapture actuator 150. With this but one acceptable construction, the deployment actuator 144 can be operated to effectuate axial movement of the delivery sheath assembly 36 relative to the inner shaft assembly 34. Similarly, the recapture actuator 150 can be manipulated to axially slide the inner shaft assembly 34 in a proximal direction relative to the delivery sheath assembly 36. In particular, the recapture actuator 150 can be axially slid relative to the housing 140, transmitting proximal forces to the inner shaft assembly 34 and, in turn, the prosthetic heart valve coupled thereto. As such, the prosthetic heart valve can be recaptured by capsule 40 for repositioning at a target site and/or retraction from a patient.

In one embodiment, recapture is facilitated by simultaneously providing distal forces to delivery sheath capsule 40 (i.e., by pushing actuator 144 relative to housing 140) as indicated by arrow 152 and proximal forces to inner shaft assembly 34 (i.e., by pulling actuator 150 relative to housing 140) as indicated by arrow 154 (e.g., in a direction opposite to distal forces 152). In this embodiment, a ratio of distal forces 152 (i.e., applied to deployment actuator 144) to proximal forces 154 (i.e., applied to recapture actuator 150) can be varied to provide forces necessary to facilitate recapture. For example, in one example, the distal forces 152 can be 25% of the recapture force while the proximal forces 154 are 75% of the recapture force. In another example, the ratio can be 50% distal forces 152 and 50% proximal forces 154. In yet another example, the ratio can be distributed to be approximately 25% distal forces 152 and approximately 75% proximal forces 154. Other ratios can further be employed.

FIG. 3A illustrates, in simplified form, loading of a prosthetic heart valve 160 within the delivery system 30. In the loaded state of FIG. 3A, the prosthetic heart valve (also referred to as a prosthesis) 160 is crimped over the inner shaft assembly 34, such that the prosthetic heart valve 160 engages the coupling structure 120. The capsule 40 compressively contains the prosthetic heart valve 160 in the compressed arrangement. Actuators 144 and 150 are coupled to housing 140 (schematically shown), which includes a proximal end 162 and a distal end 164. As discussed above, deployment actuator 144 is coupled to delivery sheath assembly 36 and configured to move the delivery sheath assembly 36 relative to inner shaft assembly 34. In particular, in order to move delivery sheath assembly 36 with respect to inner shaft assembly 34, actuator 144 can be moved toward proximate end 162 of housing 140 (i.e., causing proximal movement of capsule 40) and/or toward distal end 164 of housing 140 (i.e., causing distal movement of capsule 40). Likewise, recapture actuator 150 is coupled to inner shaft assembly 34 and thus prosthetic heart valve 160 to move the inner shaft assembly 34 relative to the delivery sheath assembly 36. In particular, actuator 150 can be moved away from proximal end 162 of housing 140 to apply proximal forces to prosthetic heart valve 160 and toward proximal end 162 to apply distal forces to inner shaft assembly 34 and prosthetic heart valve 160.

To deploy the prosthetic heart valve 160 from the delivery system 30, the delivery sheath assembly 36 is withdrawn from over the prosthetic heart valve 160, for example by proximally retracting the capsule 40 by operating actuator 144 toward proximal end 162 of housing 140, such that the capsule distal end 134 is proximal the coupling structure 120. Once the capsule 40 is proximal the coupling structure 120, the prosthetic heart valve 160 is allowed to self-expand to a natural arrangement thereby releasing from the delivery system 30.

In some instances, a clinician may desire to only partially deploy the prosthetic heart valve 160 and then evaluate before fully releasing the prosthetic heart valve 160. For example, the delivery system 30 loaded with the prosthetic heart valve 160 can be employed as part of a method to repair a damaged heart valve of a patient. Under these circumstances, the delivery system 30, in the loaded state, is advanced toward the native heart valve implantation target site, for example in a retrograde approach, through a cut-down to the femoral artery and into the patient's descending aorta. The delivery system 30 is then advanced using tip 110, under fluoroscopic guidance, over the aortic arch, through the ascending aorta, and midway across the defective aortic valve (for aortic valve replacement).

Once positioning of the delivery system 30 is estimated, the delivery sheath assembly 36, and in particular the capsule 40, is partially retracted relative to the prosthetic heart valve 160 as shown in FIG. 3B. In particular, a force as indicated by arrow 166 is applied to actuator 144 to slide the actuator 144 toward proximal end 162 of housing 140. A distal region 170 of the prosthetic heart valve 160 is thus exteriorly exposed relative to the capsule 40 and self-expands. In the partially deployed arrangement of FIG. 3B, however, at least a proximal region 172 of the prosthesis 160 remains within the confines of the capsule 40, and thus coupled to the delivery system 30. As shown in FIG. 3C, further operation of actuator 144 due to a force indicated by arrow 174 that moves actuator 144 toward proximal end 162 of housing 140 exposes a larger distal region 170 of prosthesis 160 whereas a small proximal region 172 remains within capsule 40. In this partially deployed state, a position of the stented prosthetic heart valve 160 relative to the desired implantation site can again be evaluated.

In the event the clinician believes, based upon the above evaluation, that the prosthesis 160 should be repositioned relative to the implantation site, the prosthetic heart valve 160 must first be contracted and "resheathed" by transitioning the delivery system 30 to a recapturing state. As shown in FIG. 3D, the prosthetic heart valve 160 and inner shaft assembly 34, along with tip 110 and coupling structure 120, are proximally advanced relative to the capsule 40 by operating actuator 150 away from proximal end 162, as indicated by arrow 180. In particular, proximal advancement of the prosthetic heart valve 160 causes the capsule 40 to be maneuvered into contact with the exposed distal region 170 of the prosthetic heart valve 160. The capsule 40 readily slides along a surface of the prosthetic heart valve 160. In a further embodiment, distal advancement of the capsule 40 can also be provided by operation of actuator 144 away from proximal end 162 of housing 140, such force being indicated by arrow 182. By application of force 180, potential trauma caused by exposed distal region 170 can be reduced, as further distal forces can cause distal region 170 to become further embedded in tissue of a target site (e.g., the aortic arch). As discussed above, the recapture of prosthetic heart valve 160 can further be facilitated by advancing stability layer 32 in addition to, or in replacement of, capsule 40 so as to promote recapture of prosthetic heart valve 160. In this embodiment, layer 32 can provide columnar strength to recapture valve 160. Stability layer 32 can be controlled by actuator 144 or a separate actuator, as desired.

Distal advancement of the capsule 40 and proximal advancement of the prosthetic heart valve 160 continues until capsule 40 encloses prosthetic heart valve 160, as shown in FIG. 3E. In particular, actuator 150 is further advanced away from proximal end 162 of housing 140 due to a force indicated by arrow 184. In one embodiment, the force 184 is simultaneously accompanied with a force indicated by arrow 186 on actuator 144 away from proximal end 162 of housing 140. While the distal region 170 may or may not slightly compress in response to placement within the capsule 40, complete compression of the prosthetic heart valve 160 does not occur. However, due to the combined forces 184 and 186, compressive forces required to recapture the prosthetic heart valve 160 are achieved. As shown in FIG. 3E, the capsule 40 is distally advanced to a recapturing state, forming an enclosed region that can be repositioned and/or retracted.

Once the prosthetic heart valve 160 is recaptured, the delivery system 30 can be repositioned relative to the implantation site, and the process repeated until the clinician is comfortable with the achieved positioning. Alternatively, the resheathed prosthetic heart valve 160 can be removed from the patient.

The systems and methods of the present disclosure provide a marked improvement over previous designs. By providing separate actuators for the delivery sheath capsule and the inner shaft assembly, a partially deployed prosthesis is more readily recaptured.

Although the present disclosure has been described with reference to preferred embodiments, workers skilled in the art will recognize that changes can be made in form and detail without departing from the spirit and scope of the present disclosure.

What is claimed is:

1. A method of recapturing a deployed stented prosthetic heart valve at an implantation site, the method comprising:

receiving a delivery system loaded with a radially expandable prosthetic heart valve having a frame to which a valve structure is attached, the delivery system comprising an outer sheath over an inner sheath, the inner sheath containing the prosthetic heart valve in a compressed arrangement over an inner shaft assembly in a loaded state of the delivery system;

delivering the prosthetic heart valve in the compressed arrangement through a bodily lumen of a patient and to the implantation site via the delivery system in the loaded state;

proximally retracting the inner sheath relative to the prosthetic heart valve such that a distal region of the prosthetic heart valve is exposed distal the inner sheath, wherein the distal region self-expands toward a deployed arrangement;

evaluating a position of the prosthetic heart valve relative to the implantation site;

distally advancing the outer sheath relative to the prosthetic heart valve such that the outer sheath is arranged over the prosthetic heart valve to cause the distal region of the prosthetic heart valve to transition toward a collapsed arrangement to recapture the prosthetic heart valve within the outer sheath, and proximally advancing the inner shaft assembly simultaneously with distally advancing the outer sheath to position the outer sheath over the distal region of the prosthetic heart valve to transition toward the collapsed arrangement to recapture the prosthetic heart valve within the outer sheath.

2. The method of claim 1, further comprising: proximally retracting the outer and inner sheaths from the recaptured prosthetic heart valve such that the prosthetic heart valve self-deploys from the inner shaft assembly.

3. The method of claim 1, wherein the outer sheath provides stability to the delivery system.

4. The method of claim 1, wherein the inner sheath comprises a capsule for containing the prosthetic heart valve in the compressed arrangement over the inner shaft assembly in the loaded state of the delivery system.

5. The method of claim 4, wherein the outer sheath is configured to slide over the capsule.

6. The method of claim 1, wherein the delivery system further comprises a handle comprising: a first actuator operable to proximally retract the inner sheath relative to the prosthetic heart valve; and a second actuator operable to distally advance the outer sheath relative to the heart valve.

7. The method of claim 6, wherein the handle further comprises a third actuator operable to proximally retract the inner shaft assembly relative to the inner and outer sheaths.

8. The method of claim 1, wherein the delivery system includes a handle having a housing that maintains a first actuator operable relative to the housing to apply forces to the outer sheath, a second actuator operable relative to the housing to apply forces to the inner sheath, and a third actuator operable relative to the housing to apply forces to the inner shaft assembly.

9. The method of claim 1, wherein the outer sheath can form a funnel shape at a distal end.

10. A method of recapturing a deployed stented prosthetic heart valve at an implantation site, the method comprising:

receiving a delivery system loaded with a radially expandable prosthetic heart valve having a frame to which a valve structure is attached, the delivery system comprising an outer sheath over an inner sheath, the inner sheath containing the prosthetic heart valve in a compressed arrangement over an inner shaft assembly in a loaded state of the delivery system;

delivering the prosthetic heart valve in the compressed arrangement through a bodily lumen of a patient and to the implantation site via the delivery system in the loaded state;

proximally retracting the inner sheath relative to the prosthetic heart valve such that a distal region of the prosthetic heart valve is exposed distal the inner sheath, wherein the distal region self-expands towards a deployed arrangement;

evaluating a position of the prosthetic heart valve relative to the implantation site;

distally advancing the outer sheath relative to the prosthetic heart valve such that the outer sheath is arranged over the prosthetic heart valve to cause the distal region of the prosthetic heart valve to transition toward a collapsed arrangement to recapture the prosthetic heart valve within the outer sheath; and advancing the inner sheath relative to the prosthetic heart valve such that the inner and outer sheaths are both arranged over the prosthetic heart valve to cause the distal region of the prosthetic heart valve to transition toward the collapsed arrangement to recapture the prosthetic heart valve within the inner and outer sheaths.

11. The method of claim 10, further comprising: proximally retracting the inner shaft assembly simultaneously with distally advancing the inner and outer sheaths to position the inner and outer sheaths over the distal region of the prosthetic heart valve to transition toward the collapsed arrangement to recapture the prosthetic heart valve within the inner and outer sheaths.

12. A method of deploying a stented prosthetic heart valve at an implantation site, the method comprising:

loading a prosthetic heart valve into a delivery system, the delivery system comprising an outer sheath assembly configured to be slidably disposed over an inner sheath assembly such that a distal region of the inner sheath assembly is exposed distal the outer sheath, the inner sheath assembly configured to be slidably disposed over an inner shaft assembly, a distal region of the inner sheath assembly containing the prosthetic heart valve in a compressed arrangement over the inner shaft assembly;

delivering the prosthetic heart valve in the compressed arrangement through a bodily lumen of a patient and to the implantation site via the delivery system in the loaded state;

proximally retracting the inner sheath relative to the prosthetic heart valve such that a distal region of the prosthetic heart valve is exposed distal the inner sheath, wherein the distal region self-expands toward a deployed arrangement;

evaluating a position of the prosthetic heart valve relative to the implantation site;

distally advancing the outer sheath relative to the prosthetic heart valve such that the outer sheath is arranged over the prosthetic heart valve to cause the distal region of the prosthetic heart valve to transition toward a collapsed arrangement within the outer sheath;

proximally retracting the outer sheath from the collapsed prosthetic heart valve;

proximally retracting the inner sheath from the collapsed prosthetic heart valve such that the prosthetic heart valve self-deploys from the inner shaft assembly; and distally advancing the inner and outer sheaths relative to the prosthetic heart valve such that the inner and outer sheaths are arranged over the prosthetic heart valve to cause the distal region of the prosthetic heart valve to transition toward the collapsed arrangement within the inner and outer sheaths.

13. The method of claim 12, wherein the delivery system further comprises a handle comprising: a first actuator operable to proximally retract the inner sheath relative to the prosthetic heart valve; and a second actuator operable to distally advance the outer sheath relative to the heart valve.

14. The method of claim 13, wherein the handle further comprises a third actuator operable to proximally retract the inner shaft assembly relative to the inner and outer sheaths.

15. The method of claim 12, wherein the delivery system includes a handle having a housing that maintains a first actuator operable relative to the housing to apply forces to the outer sheath, a second actuator operable relative to the housing to apply forces to the inner sheath, and a third actuator operable relative to the housing to apply forces to the inner shaft assembly.

16. The method of claim 12, wherein the outer sheath can form a funnel shape at a distal end.

17. A method of deploying a stented prosthetic heart valve at an implantation site, the method comprising:
    loading a prosthetic heart valve into a delivery system, the delivery system comprising an outer sheath assembly configured to be slidably disposed over an inner sheath assembly such that a distal region of the inner sheath assembly is exposed distal the outer sheath, the inner sheath assembly configured to be slidably disposed over an inner shaft assembly, a distal region of the inner sheath assembly containing the prosthetic heart valve in a compressed arrangement over the inner shaft assembly;
    delivering the prosthetic heart valve in the compressed arrangement through a bodily lumen of a patient and to the implantation site via the delivery system in the loaded state;
    proximally retracting the inner sheath relative to the prosthetic heart valve such that a distal region of the prosthetic heart valve is exposed distal the inner sheath, wherein the distal region self-expands toward a deployed arrangement;
    evaluating a position of the prosthetic heart valve relative to the implantation site;
    distally advancing the outer sheath relative to the prosthetic heart valve such that the outer sheath is arranged over the prosthetic heart valve to cause the distal region of the prosthetic heart valve to transition toward a collapsed arrangement within the outer sheath;
    proximally retracting the outer sheath from the collapsed prosthetic heart valve;
    proximally retracting the inner sheath from the collapsed prosthetic heart valve such that the prosthetic heart valve self-deploys from the inner shaft assembly; and
    proximally advancing the inner shaft assembly simultaneously with distally advancing the outer sheath to position the outer sheath over the distal region of the prosthetic heart valve to transition toward the collapsed arrangement to recapture the prosthetic heart valve within the outer sheath.

18. A method of deploying a stented prosthetic heart valve at an implantation site, the method comprising:
    loading a prosthetic heart valve into a delivery system, the delivery system comprising an outer sheath assembly configured to be slidably disposed over an inner sheath assembly such that a distal region of the inner sheath assembly is exposed distal the outer sheath, the inner sheath assembly configured to be slidably disposed over an inner shaft assembly, a distal region of the inner sheath assembly containing the prosthetic heart valve in a compressed arrangement over the inner shaft assembly;
    delivering the prosthetic heart valve in the compressed arrangement through a bodily lumen of a patient and to the implantation site via the delivery system in the loaded state;
    proximally retracting the inner sheath relative to the prosthetic heart valve such that a distal region of the prosthetic heart valve is exposed distal the inner sheath, wherein the distal region self-expands toward a deployed arrangement;
    evaluating a position of the prosthetic heart valve relative to the implantation site;
    distally advancing the outer sheath relative to the prosthetic heart valve such that the outer sheath is arranged over the prosthetic heart valve to cause the distal region of the prosthetic heart valve to transition toward a collapsed arrangement within the outer sheath;
    proximally retracting the outer sheath from the collapsed prosthetic heart valve;
    proximally retracting the inner sheath from the collapsed prosthetic heart valve such that the prosthetic heart valve self-deploys from the inner shaft assembly; and
    distally advancing the inner sheath relative to the prosthetic heart valve such that the inner and outer sheaths are both arranged over the prosthetic heart valve to cause the distal region of the prosthetic heart valve to transition toward the collapsed arrangement within the inner and outer sheaths.

19. The method of claim 18, further comprising: proximally retracting the inner shaft assembly simultaneously with distally advancing the inner and outer sheaths to position the inner and outer sheaths over the distal region of the prosthetic heart valve to transition toward the collapsed arrangement within the inner and outer sheaths.

* * * * *